United States Patent

Bull

Patent Number: 5,732,862
Date of Patent: Mar. 31, 1998

[54] MATERIAL HOLDING APPARATUS WITH INTEGRATED FINGER MOUNT

[76] Inventor: Charles L. Bull, 1100 Bluff Dr., Osage Beach, Mo. 65065

[21] Appl. No.: 800,754

[22] Filed: Feb. 14, 1997

[51] Int. Cl.⁶ .................................................. A41D 19/00
[52] U.S. Cl. .................... 224/217; 224/148.1; 63/1.14; 63/15; 206/63.5; 433/163; 248/311.2
[58] Field of Search ........................... 224/191, 217, 224/414, 926, 148.1, 148.4, 148.7; 63/15, 15.1, 1.11, 1.14; 206/63.5; 433/49, 97, 163; 248/311.2

[56] References Cited

U.S. PATENT DOCUMENTS

| | | | |
|---|---|---|---|
| 902,109 | 10/1908 | Powell . | |
| 1,458,436 | 6/1923 | Pameyer . | |
| 1,952,203 | 3/1934 | Fox | 132/79 |
| 1,955,175 | 4/1934 | Crowther | 206/46 |
| 2,222,741 | 11/1940 | Bush | 32/1 |
| 2,356,722 | 8/1944 | Harris | 91/54.4 |
| 2,537,449 | 1/1951 | Evenson | 63/15 |
| 2,539,940 | 1/1951 | Abramson | 224/28 |
| 2,665,479 | 1/1954 | Weldon | 32/1 |
| 2,970,379 | 2/1961 | Hardgrove | 32/1 |
| 3,306,566 | 2/1967 | Paulson et al. | 248/311.2 |
| 3,327,391 | 6/1967 | Malm | 32/1 |
| 3,381,814 | 5/1968 | Benfield | 206/63.5 |
| 3,485,353 | 12/1969 | Reiter | 433/97 |
| 4,427,130 | 1/1984 | Szigeti | 63/1.14 |
| 4,717,057 | 1/1988 | Porteous | 224/217 |
| 4,844,308 | 7/1989 | Porteous | 224/217 |
| 4,901,847 | 2/1990 | Kesling | 206/63.5 |
| 4,948,080 | 8/1990 | Jack | 224/414 |
| 4,991,759 | 2/1991 | Scharf | 224/217 |
| 5,016,795 | 5/1991 | Porteous | 224/217 |
| 5,048,731 | 9/1991 | Moreschini | 224/541 |
| 5,112,227 | 5/1992 | Bull | 433/163 |
| 5,139,188 | 8/1992 | Scharf | 224/217 |
| 5,169,315 | 12/1992 | Bull | 433/163 |
| 5,249,963 | 10/1993 | McGarrigle | 433/163 |
| 5,368,482 | 11/1994 | Johnsen et al. | 433/163 |
| 5,404,731 | 4/1995 | Traub | 63/15 |
| 5,562,732 | 10/1996 | Eisneberg | 623/15 |

*Primary Examiner*—Henry J. Recla
*Assistant Examiner*—Gregory M. Vidovich
*Attorney, Agent, or Firm*—Herzog, Crebs & McGhee, LLP

[57] ABSTRACT

A material holding apparatus comprising a receptacle and an integrated finger mount. A lip or groove is circumferentially added to disposable plastic cups used in the dental profession. The receptacle preferably includes projections which mate by snap fit with either the lip or groove of the disposable cups. The finger mount is made of a flexible material and is made with two arms extending from the base of the receptacle, arcing to form a ring. The ends of the arms approach one another, but remain flexible so as to fit a wide variety of finger sizes. Alternatively, a single band may be used as the finger mount. With either embodiment, the finger mount is slipped over the finger of the use, usually a dental professional.

7 Claims, 2 Drawing Sheets

MATERIAL HOLDING APPARATUS WITH INTEGRATED FINGER MOUNT

FIELD OF THE INVENTION

The present invention relates generally to material holding apparatus and more specifically to a material holding apparatus with an integrated ring for mounting on a the finger of a user.

BACKGROUND OF THE INVENTION

Dental professionals often use liquid, gelatinous, or otherwise pasty materials in their practice such as polish, fillings, medications, and prophylactic remedies. The dentist needs quick and easy access to these materials while operating on a patient. Several devices have been developed to provide such convenient access, by putting the material directly in the hand of the dentist, rather than placing the materials on a nearby tray which would require constant turning and shifting.

One such device is shown in U.S. Pat. No. 3,327,391, to Malm. Malm discloses a finger mounted holding apparatus consisting of two parts: a base and a cup. The cup is disposable and contains the material needed by the dentist. The base is a finger ring, which is worn around the finger of the dentist. The cup is secured to the ring by a projection, preferably extending from the base which is received by a recess in the cup.

Shortcomings with Malm include a lack of stability in the apparatus during use. Furthermore, Malm requires much precision in the manufacturing of the components involved in securing the cup and the base.

Since Malm, other inventions have overcome its shortcomings, such as that disclosed in U.S. Pat. No. 5,169,315 to Bull. Bull teaches a single integrated unit with a cup which may hold material directly or hold disposable plastic cups containing the dental material. It is certainly more convenient to keep the material in disposable plastic cups which are designed for a single use, than to fill the apparatus before and wash it after each use. However, when used with the disposable cups, Bull, sacrifices the securing means, however unstable, found in Malm.

More recently, the distribution of dental materials in disposable plastic cups designed for single use has become commonplace. The cups that are used for this purpose come with a foil seal which is peeled off just before use. They are generally plastic molded cups.

Accordingly, it is the primary object of this invention to provide a material holding apparatus with an integrated finger mount which securely holds the disposable cups used today in the dental profession.

It is another object of this invention to hold the disposable cups in a stable manner.

It is yet another object of this invention to adapt plastic disposable cups for the purpose of allowing a secure and stable fit. Other objects and features will be in part pointed out hereinafter.

SUMMARY OF THE INVENTION

In keeping with the above, the present invention is a single integrated unit. One part of the unit consists of a ring to be worn on the finger of a dental professional when using materials such as prophylactic remedies or other substances contained in disposable plastic cups. The other part of the unit consists of a receptacle permanently mounted on top of the ring, which in the preferred embodiment is designed to mate with disposable plastic cups using a snap fit.

The disposable plastic cups may contain any sort of material used in a dental practice, and are designed to carry only enough for a single use. The top is sealed, usually with aluminum foil, polyethylene clear, polyethylene with paper backing, or similar seal. The cups have either a circumferential groove or alternately a lip.

In the preferred embodiment, the receptacle is a cylinder with a concentric cavity in the top for receiving the cup. The cavity is approximately the same diameter as the groove or lip on the cup. A plurality of projections are disposed on the inside wall of the cavity. The projections are preferably integrated with the remainder of the receptacle during the molding process.

When a cup is placed in the receptacle during use, the lip of the cup will snap fit underneath the projections. If a cup with a groove is used, the projections snap fit therein. Following its use, the cup can be separated from the receptacle with a firm pull, or alternatively the entire ring may be disposed of with the cup after one use.

In an alternative embodiment, the projections may be omitted. In this case, the side wall of the cavity slopes radially inward to produce a friction or interference fit. This embodiment, however, lacks the level of stability provided with the snap fit from the projections.

The finger mount or ring portion of the unit is created together with the receptacle portion during the molding process. A wide variety of materials may be used for the apparatus, namely any material that may be molded, preferably some type of plastic such as polyethylene, polypropylene, or copolymers of polyethylene and polypropylene.

The finger mount may take a variety of forms. The preferred forms include either arms or a band extending from the receptacle to create a ring. To accommodate a variety of individual finger sizes, the arms or band should be flexible and the ring formed should not be completely closed. If a pair of arms are used, the arms should create opposing semi-circles which approach each other, but do not touch, or at the very least are separable at the ends furthest from the receptacle.

During use, the present plastic cup containing the desired material is snapped into the receptacle. The finger mount is then slipped over the thumb or finger of the user. Following use, the cup is removed from the receptacle and disposed of. Optionally, the entire apparatus may be disposed of after each use, due to the inexpensive manufacturing thereof.

It should also be noted that the holding apparatus may be used for applications other than dentistry. A number of other materials, such as paint, may be stored in the disposable plastic cups and used with the present invention.

BRIEF DESCRIPTION OF THE DRAWINGS

So that the manner in which the above-recited features, advantages, and objects of the present invention are attained and can be understood in detail, a more particular description of the invention, briefly summarized above, may be had by reference to the embodiments thereof which are illustrated in the appended drawings.

It is noted, however, that the appended drawings illustrate only several typical embodiments of this invention and is therefore not to be considered limiting of its scope, for the invention may admit to other equally effective embodiments. Reference the appended drawings, wherein.

DETAILED DESCRIPTION OF THE DRAWINGS

Figure 1:
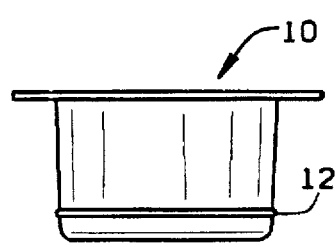
FIG. 1A is a side elevation of a disposable cup having a lip used in accordance with the present invention for storing dental materials.
FIG. 1B is a side elevation of a disposable cup having a groove used in accordance with the present invention for storing dental materials.
Figure 1A:
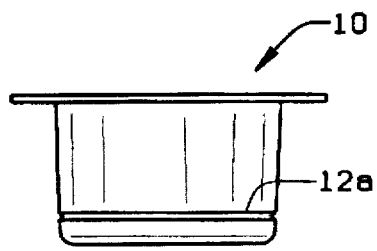

Referring now to FIG. 1, a disposable plastic cup 10, in accordance with the present invention is shown generally. The cup 10 is used to hold a wide variety of materials, particularly related to the dental profession. The cup 10 is round with a lip 12 circumferentially circling it near the bottom. In some cases, the lip 12 is replaced with a groove 12a as shown in FIG. 1B (not shown).

Figure 2:
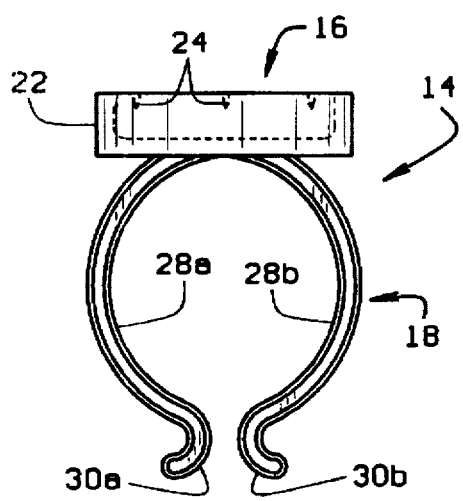
FIG. 2 is a side view of an embodiment of the present finger mount with receptacle.
Figure 2A:
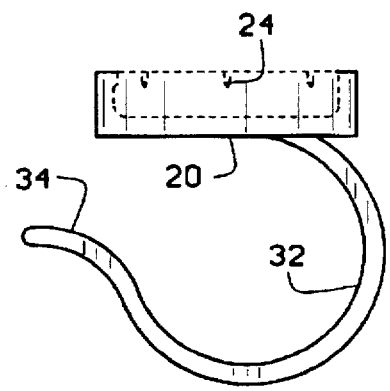
FIG. 2A is a side view of the present invention with a "band" finger mount.
Figure 3:
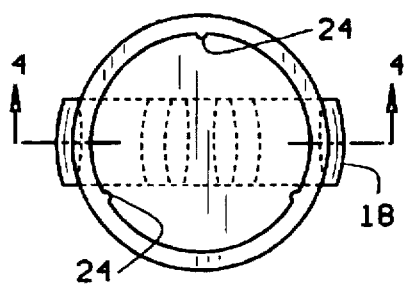
FIG. 3 is a top view of the present invention in its preferred embodiment.
Figure 3A:
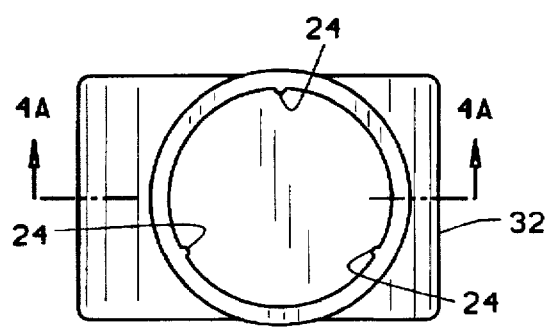
FIG. 3A is a top view of the present invention with a "band" finger mount.
Figure 4:
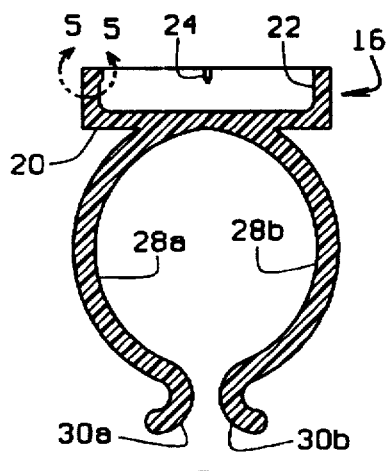
FIG. 4 is cross-section along line 4—4 of the present invention in its preferred embodiment.
Figure 4A:
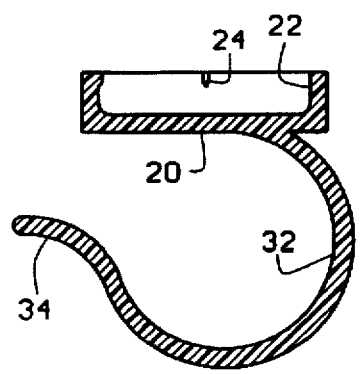
FIG. 4A is a cross-section along line 4A—4A of the present invention with a "band" finger mount.

FIGS. 2, 3, and 4 show the present invention, a material holding apparatus 14 for use with the cup 10. Although created simultaneously and molded together, the apparatus consists of two parts: a receptacle 16 and a finger mount 18. In the preferred embodiment the receptacle is essentially a round base 20, with a side wall 22 radially extending from the base 20. A plurality of projections 24 are disposed about the side wall 22, preferably near the top of the side wall 22 and evenly spaced with relation to one another. A minimum of three projections 24 should be used, but more a fewer projections may suffice.

Figure 5:
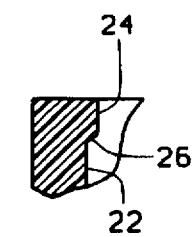
FIG. 5 is an enlarged cross-sectional view of a projection in accordance with the present invention about the arc 5—5.
Figure 6:
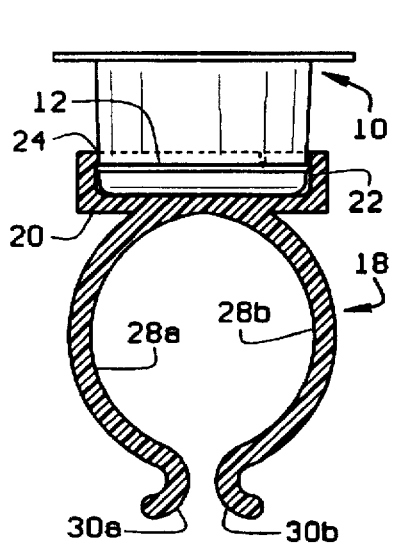
FIG. 6 is a side view in partial cross-section of the present invention securing a disposable cup of a dental material in the preferred embodiment.
Figure 6A:
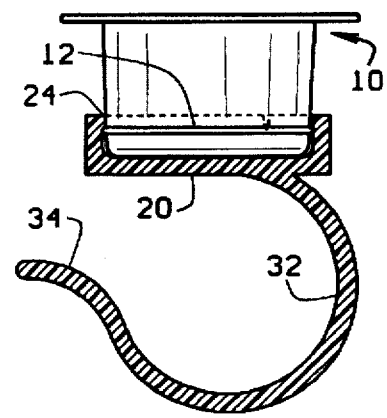
FIG. 6A is a side view in partial cross-section of the present invention securing a disposable cup of a dental material with a "band" finger mount.

FIG. 5 shows an enlarged sectional view of one of the projections 24. The projections 24 should each be approximately ⅟₃₂" in height so as to fit within the groove of a cup 10, should such an embodiment of the cup 10 be used. The projections 24 should each reach out approximately 0.01" from the side wall 22, and have a 45 degree bevel 26 on the bottom side. When the embodiment of the cup 10 with a lip 12 is used, the lip 12 snap fits with the projections 24, resting underneath the bevel 26, as seen in FIG. 6.

The finger mount in the preferred embodiment is composed of a pair of arms 28a and b respectively. The arms extend from the base 20 in opposing directions and arc around to form a ring, just shy of closure. The ends of the arms 28a and b may touch, but must be kept separate during the molding process. The arms 28a and b should be flexible to allow them to fit over a wide range of finger sizes. Optionally, the ends of the arms 28a and b should be bent back into tails 30a and b respectively to reduce the risk of injury to the finger during use.

An alternate finger mount is shown in FIGS. 2A, 3A, 4A, and 6A respectively. The alternate finger mount consists of a single band 32 extending from the base 20. As can be seen in the top view of FIG. 3A, the band 32 is considerably wider (approximately ⅝ total width) than the arms 28a and b of the preferred embodiment. The band 32 arcs around, starting tangentially with the base 20, and extending approximately 270 degrees. The band 32 then ends in a tail 34 arcing in the opposite direction of the main part of the band 32. Again, the band 32 should be flexible so as to fit a variety of finger sizes.

Figure 7:
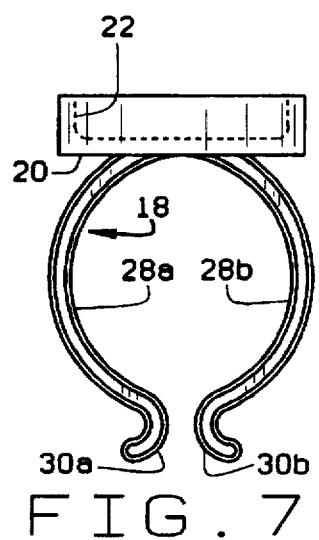
FIG. 7 is a side elevation of the present invention designed to use a friction fit for securing the dental material.
Figure 8:
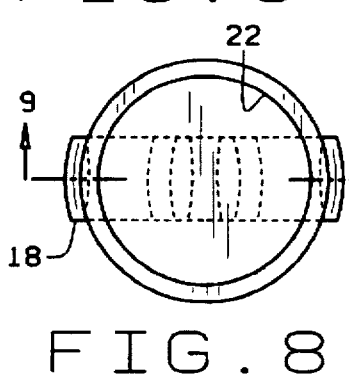
FIG. 8 is a top view of the present invention designed to use a friction fit for securing the dental material.
Figure 9:
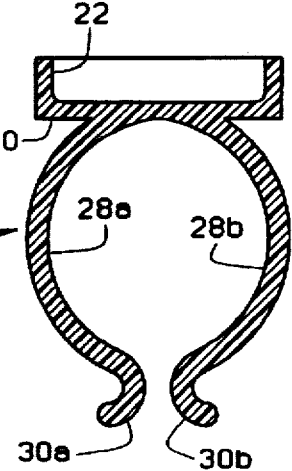
FIG. 9 is a cross-section along line 9—9 of the present invention designed to use a friction fit for securing the dental material.

An alternative embodiment of the receptacle is shown in FIGS. 7, 8, and 9. The alternative embodiment of the receptacle is identical to the preferred, but for a lack of projections 24. The side wall 22 is sloped outward approximately 1 degree with the larger radius being at the top. In lieu of a snap fit, the cup 10 is secured to the receptacle using a friction or interference fit. The snap fit embodiment is obviously preferred due to the more secure fit than that obtained by using a friction fit.

While the foregoing is directed to the preferred embodiments of the present invention, other and further embodiments of the invention may be devised without departing from the basic scope thereof, and the scope thereof is determined by the claims which follow.

What is claimed is:

1. A material holding apparatus comprising:

a base with an upper surface and a lower surface;

a receptacle with a projecting side wall extending upward from the upper surface of said base;

a finger mount extending from the lower surface of said base; said finger mount sized to fit over a human finger;

a cup matingly received by said receptacle;

a plurality of projections extending from the side wall of said receptacle; and a lip circumferentially disposed about said cup in a position to snap fit under said projections.

2. The material holding apparatus of claim 1, wherein said lip is replaced with a groove circumferentially disposed about said cup in a position to snap fit over said projections.

3. The material holding apparatus of claim 1, wherein said cup and said receptacle are round.

4. The material holding apparatus of claim 3, wherein said finger mount consists of a pair of curved arms, said arms projecting in opposing directions from the lower surface of said base, each said arm forming an arc to come in contact with a human finger.

5. The material holding apparatus of claim 4, wherein said arms are made of a flexible material.

6. The material holding apparatus of claim 3, wherein said finger mount consists of a band tangentially extending from the lower surface of said base, said band curving to form an arc between 210 and 270 degrees, and a tail equal in width to said band, said tail arcing in the opposing direction of said band.

7. The material holding apparatus of claim 3, wherein said projections are disposed about the top of said receptacle.

* * * * *